United States Patent [19]
Robinson

[11] Patent Number: 4,816,030
[45] Date of Patent: Mar. 28, 1989

[54] INTRAOCULAR LENS

[76] Inventor: Paul J. Robinson, 625 S. Orange Grove Ave., Pasadena, Calif. 91105

[21] Appl. No.: 72,431

[22] Filed: Jul. 13, 1987

[51] Int. Cl.$^4$ ............................................. A61F 2/16
[52] U.S. Cl. ...................................................... 623/6
[58] Field of Search ........................................... 623/6

[56] References Cited

U.S. PATENT DOCUMENTS

| | | | |
|---|---|---|---|
| 4,244,060 | 1/1981 | Hoffer | 623/6 |
| 4,446,581 | 5/1984 | Blake | 623/6 |
| 4,494,254 | 1/1985 | Lopez | 623/6 |
| 4,536,895 | 8/1985 | Bittner | 623/6 |
| 4,629,462 | 12/1986 | Feaster | 623/6 |
| 4,676,794 | 1/1987 | Kelman | 623/6 |

FOREIGN PATENT DOCUMENTS 667206  6/1979  U.S.S.R. ................................... 623/6

Primary Examiner—Ronald L. Frinks
Attorney, Agent, or Firm—Charles H. Schwartz; Ellsworth R. Roston

[57] ABSTRACT

An intraocular lens is adapted to be implanted within an eye adjacent the iris of the eye in either the anterior or posterior position or inside the lens capsule. The intraocular lens includes a lens portion and at least one flexible fixation device carried by the lens portion. The fixation device provides supportive engagement with the eye structure in either the anterior or posterior position or inside the lens capsule to centrally position the intraocular lens portion within the eye structure. The flexible fixation device is formed as a flexible loop attached to the intraocular lens portion and with the loop formed by a coil spring.

18 Claims, 4 Drawing Sheets

U.S. Patent  Mar. 28, 1989  Sheet 1 of 4  4,816,030
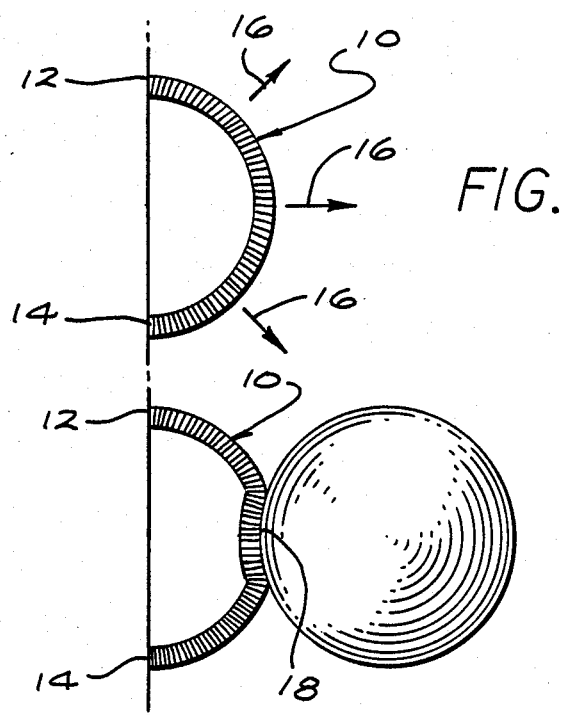
FIG. 1A
FIG. 1B
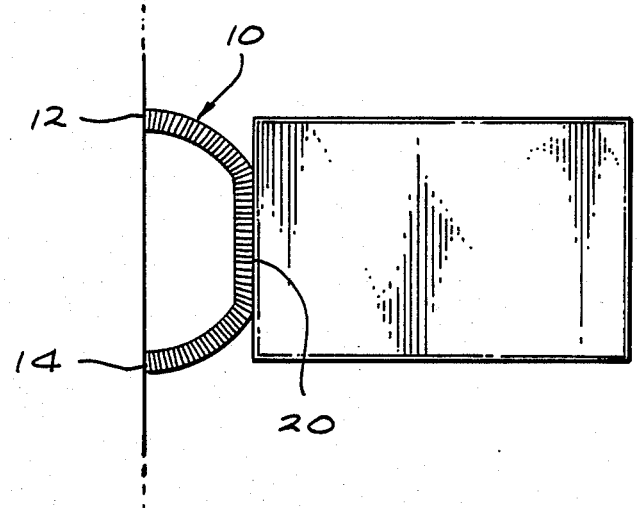
FIG. 1C

INTRAOCULAR LENS

BACKGROUND OF THE INVENTION

1. Field of the Invention

The present invention relates to an intraocular lens and specifically an intraocular lens which may be implanted in the anterior or posterior chamber or in the lens capsule of the eye after removal of the cataract from the natural lens of an eye as a result of a cataract condition or after removal of the natural lens.

2. Description of the Prior Art

Cataract surgery in general involves the removal of the lens or lens nucleous from the eye of a patient. After removal of the clouded material, a commom procedure is to implant within the eye an artificial lens known as an intraocular lens. The intraocular lens may be supported in either the anterior or posterior chamber of the eye or in the lens capsule. In general, the intraocular lenses currently used have the lens supported by wires or flexible loops which extend from the lens outwardly to contact circumferential groove anterior or posterior portions of the eye adjacent the iris or to contact the inside diameter of the lens capsule.

The current types of intraocular lenses are generally characterized by a central lens or lenticular portion and two or more radially resilient wires or loops which extend outwardly of the lens. These wires or loops theoretically engage the circumferential eye structure gently but elastically so as to centrally locate the lens portion. The disadvantage with these wires or loops is that they continuously exert pressure on the centrifical eye structures which pressure can produce discomfort and potential damage to the eye. The pressure is enhanced since typically the contact is at a limited number of contact points in the circumferential groove portions. Some of the earlier intraocular lenses have contact at only a single point and this has caused particular difficulty. Later designs for intraocular lenses have attempted to increase the number of points at which the lens is supported in the anterior or posterior cylindrical eye portions or in the lens capsule. One difficulty is that the anterior and posterior cylindrical eye portions do not present a pure cylindrical curvature so that no matter what design is proposed for the loops or wires, there can be individual points of great pressure.

Many prior art structures have attempted to overcome the above difficulty by providing for a large variety in loop structures having either closed or open ends and having greater or lesser degrees of flexibility. If the loops are too flexible, the lens may not be maintained properly in a centered position. If the loops are too rigid, then the above problem of creating too much force at a small number of points can occur.

One attempt to overcome the above problems may be seen with reference to Hoffer Pat. No. Re. 31,626. This patent includes a detailed background description discussing in general the genesis of intraocular lenses and describing various types of self centering lenses using flexible loops. In the Hoffer patent, an attempt is made to overcome the problems of the prior art by using a plurality of pliant lens centering filaments extending outwardly to center the lens within the eye structure. It can be seen that although the Hoffer patent does increase the number of contact points by using a large plurality of filaments, still, any one or more individual filaments may exert significantly more pressure at a particular point or points. This is because the filaments operate independently and are preformed to a particular size and shape so that the filaments as a group may not readily adapt to an irregular surface within the eye. Additionally, the Hoffer patent is specifically designed as a posterior chamber lens and may not be useful as an anterior chamber lens.

SUMMARY OF THE INVENTION

The present invention provides for an intraocular lens using a compression spring to support the intraocular lens. Specifically, the compression spring is formed as a helical member which can exactly follow the curvature of the anterior or posterior chambers of the eye. The spring therefore appears as a coil formed of very fine suture material to follow any irregular shape or surface that the spring comes in contact with.

Because the spring is formed of very fine material, the load or weight of the intraocular lens is widely distributed over a large number of points in either the anterior or posterior circumferential portions or inside the lens capsule. Moreover, the load will be evenly distributed since the coil will adjust to any irregular surfaces so that in addition to having the load distributed over a large number of points, it is also evenly distributed within these different points. The structure of the present invention produces the best combination of flexibility and pressure distribution so that the lens will be maintained in the center position and will be maintained in that position with the same even distribution of pressure even if the lens is displaced after insertion. For example, if any rotation of the lens occurs, the same even distribution of the pressure over a large number of points will occur.

As indicated above, the coil may be formed from a plastic suture material. This plastic material may be a polypropylene material. The coil structure of the present invention may be used with any type of intraocular lens currently in use. For example, the coil mounting may be used with a normal lens or a foldable lens which foldable lens enhances the insertability of the lens. Even with a normal lens, the coil spring can adapt its position and the lens will be easy to insert since the surgeon does not have to be concered about distorting the configuration of the coil spring. This is in distinction to the currently used lenses with loops wherein the surgeon must be concerned with not distorting the loop past its elastic limit. It will be appreciated that if a loop is distorted then the lens will then not be properly centered. The present invention overcomes this problem since the coils are very flexible and easily adapt to the necessary shape for insertion and then return to the desired shape to support the lens in the proper position in the eye.

DETAILED DESCRIPTION OF THE DRAWINGS

A clearer understanding of the present invention will be had with reference to the following description and drawings wherein;

FIG. 1A illustrates the coil spring loop of the present invention shown in a free and expanded state;

FIG. 1B illustrates the coil spring adapting to a spherical surface;

FIG. 1C illustrates the coil spring adapting to a flat surface;

DETAILED DESCRIPTION OF THE PREFERRED EMBODIMENTS

Figure 2:
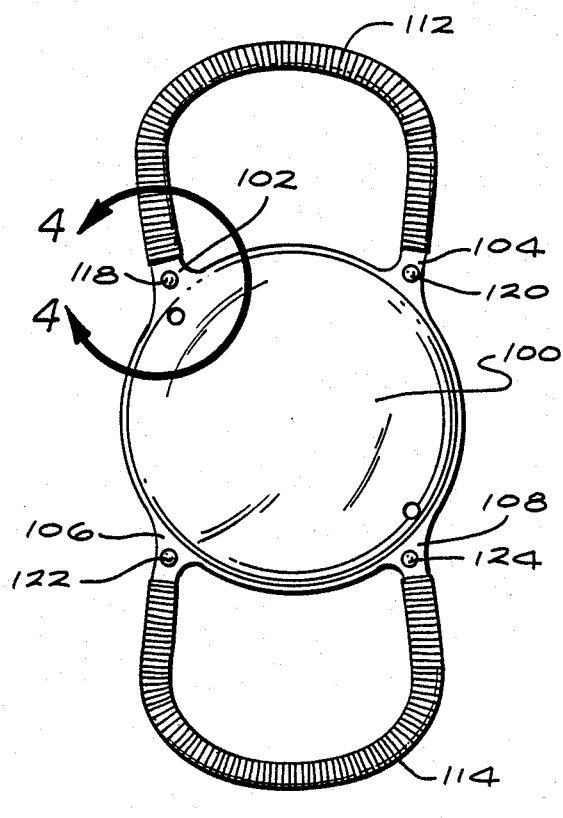
FIG. 2 illustrates a first embodiment of the invention showing a first method of attaching the coil spring loops to an intraocular lens.

As shown in FIG. 1A, a coil spring 10 may be attached at its end points 12 and 14. With such an attachment, the coil spring 10 will generally take the form of a semicircle and will exert equal radial outward forces as shown by arrows 16. The coil 10 for the purpose of the present invention may be made of a fine plastic filament material such as the type of plastic material used for sutures. Specifically, this material may be a polypropylene plastic such as the type sold by Johnson and Johnson under the Trademark PROLENE. It is also to be appreciated that the coil may be made of other types of plastic materials and may even be made of very fine metals such as stainless steel. However the preferred embodiment is the use of the polypropylene suture material currently in use. The suture material is wrapped tightly around a fine mandrel to form a helix and the helix is held in postion while the entire structure is brought up to an appropriate temperature so as to set the material into the coil shape.

The diameter of the filament wire can be very fine, such as three to six thousands, and the diameter of the helix itself may also be quite small such as two to four hundredths of an inch or smaller. In any event the coil forms a very flexible spring loop 10 which can readily adapt to almost any surface and provide for contact over a large number of points with relative uniformity of pressure at these different points. This can be seen for example with reference to FIGS. 1B and 1C where the coil 10 is shown contacting first a spherical surface 18 and a flat surface 20. In both instances, the spring rolls into the appropriate position and provides contact at a multiplicity of points and with relatively uniform pressure at these different points.

FIG. 2 illustrates a first embodiment of a intraocular lens showing the use of the coil loop as shown in FIGS. 1A through 1C. In FIG. 2, a central lens portion 100 is constructed in a normal fashion. The lens portion 100 includes extending flat post portions 102, 104, 106 and 108. Each post portion 102 through 108 includes an opening such as the opening 110 shown in FIG. 4. The openings and post portions members are used to seat and secure the coil spring loop such as the coil spring loops 112 and 114. Both of these coils spring loops would be essentially the same and constructed in the same manner as the loop 10 as shown in FIGS. 1A through 1C.

Figure 4:
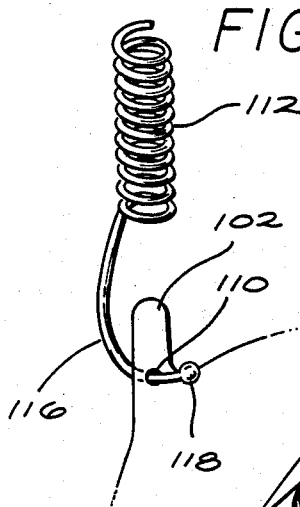
FIG. 4 illustrates a particular method of securing the ends of the coil spring loops in the first embodiment of the invention.

As shown in FIG. 4, an end portion 116 of the loop 112 is inserted through the opening 110 and with this end portion either heated or tied to form a ball 118. Similar balls 120, 122 and 124 would be formed at the other end portions of the coil spring loops 112 and 114. The coils are positioned around the posts 102 through 108 and with the ball portions 118 through 124 locking the ends of the coils 112 and 114 in position.

Figure 3:
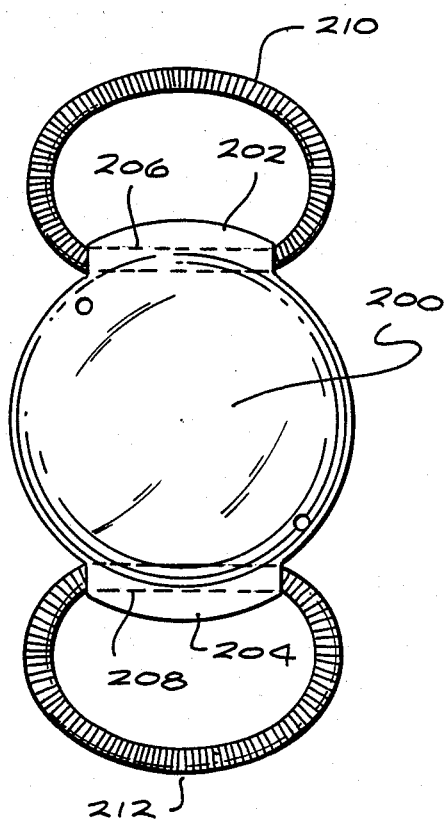
FIG. 3 is a second embodiment of the invention showing a second method of attaching coil springs loops to an intraocular lens.

FIG. 3 illustrates a second embodiment of the intraocular lens of the present invention. In FIG. 3, a central lens portion 200 is formed and with flange portions 202 and 204 extending from two sides of the central lens portion 200. Each flange portion 202 and 204 includes an opening which are openings 206 and 208.

Coil spring loops 210 and 212, which may be essentially the same as the coil springs shown in FIGS. 1A through 1C, have their end portions inserted into the openings 206 and 208. The ends of the coil springs 210 and 212 may be held within the openings in any appropriate fashion. This may include a friction fit and/or including adhesive material to lock the ends within the openings 206 and 208. In addition, the end portions of the coil springs may be interconnected and positioned within the opening. In any event, the coil springs 210 and 212 have a more circular configuration as compared with the more semi-circular configuration of the coil springs of the embodiment of FIG. 2.

Depending upon the particular structure and size of the available eye chambers and whether the lens is to be inserted in the anterior or posterior chambers or in the lens capsule, one or the other of the embodiments shown in FIGS. 2 and 3 may be more appropriate. It is also to be appreciated that other types of configurations may be used and other methods of attaching the coil springs to the central lens portion may be used. In addition, more or less than two coil springs may be used. For example, three or even four such coil springs may be positioned around the circumference of the central lens portion and it would also be possible to use only a single coil spring in association with a different type of loop structure at the other side of the lens.

Figure 5:
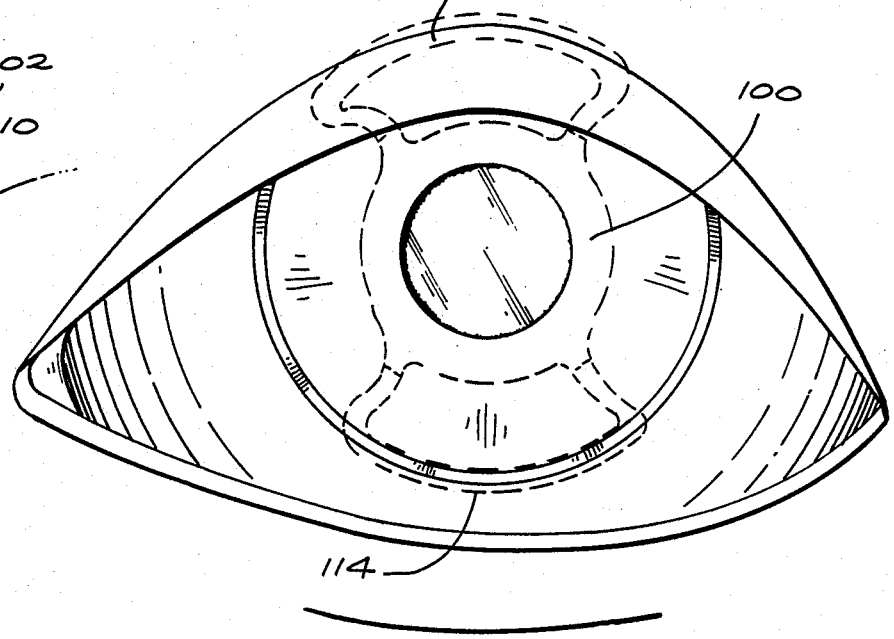
FIG. 5 illustrates a front view of the intraocular lens of the present invention as inserted into the eye.
Figures 6, 7:
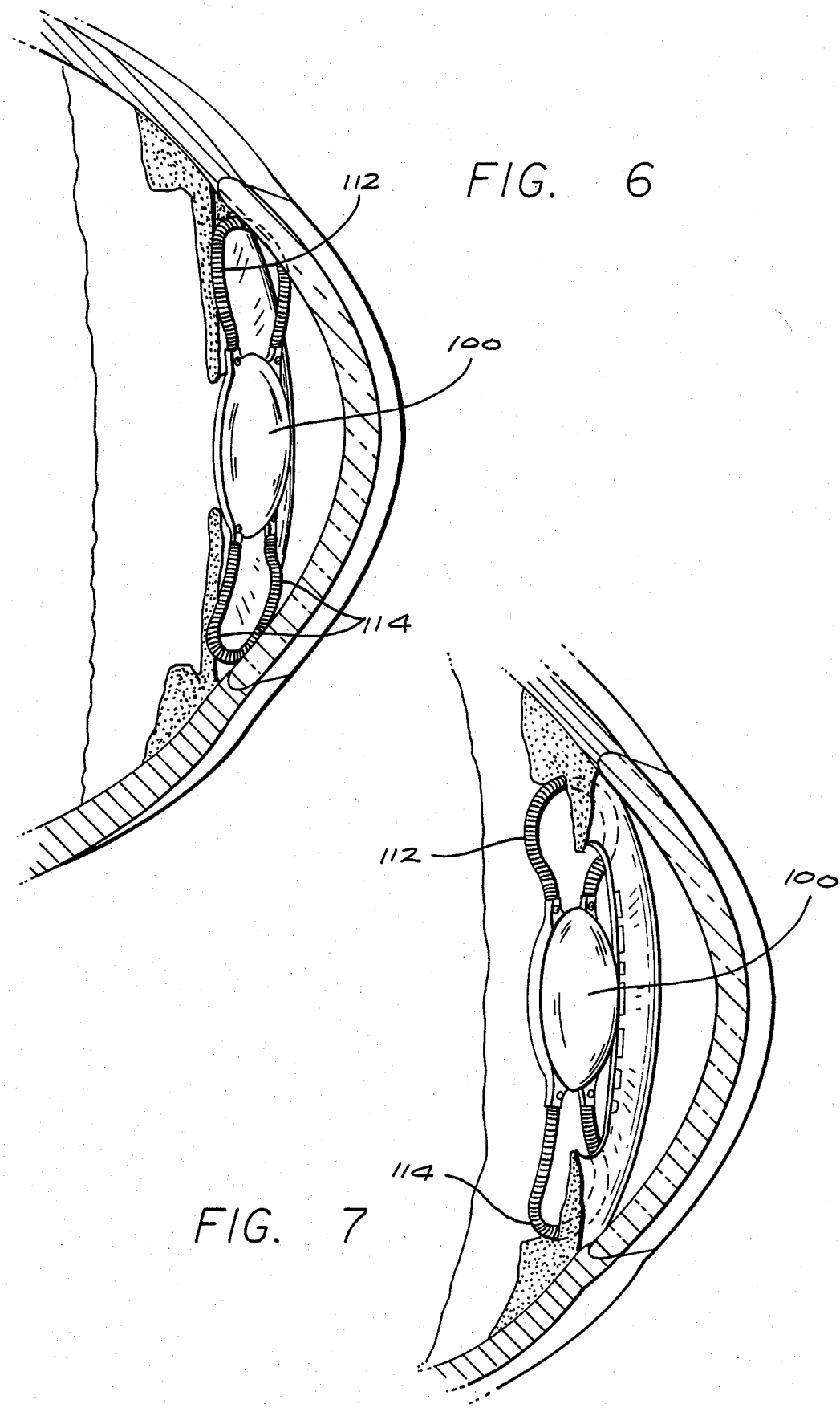
FIG. 6 illustrates a cross-sectional view of the intraocular lens of the present invention as inserted into the eye and in an anterior position.
FIG. 7 illustrates a cross-sectional view of the intraocular lens of the present invention as inserted into the eye and in a posterior position.
Figure 8:
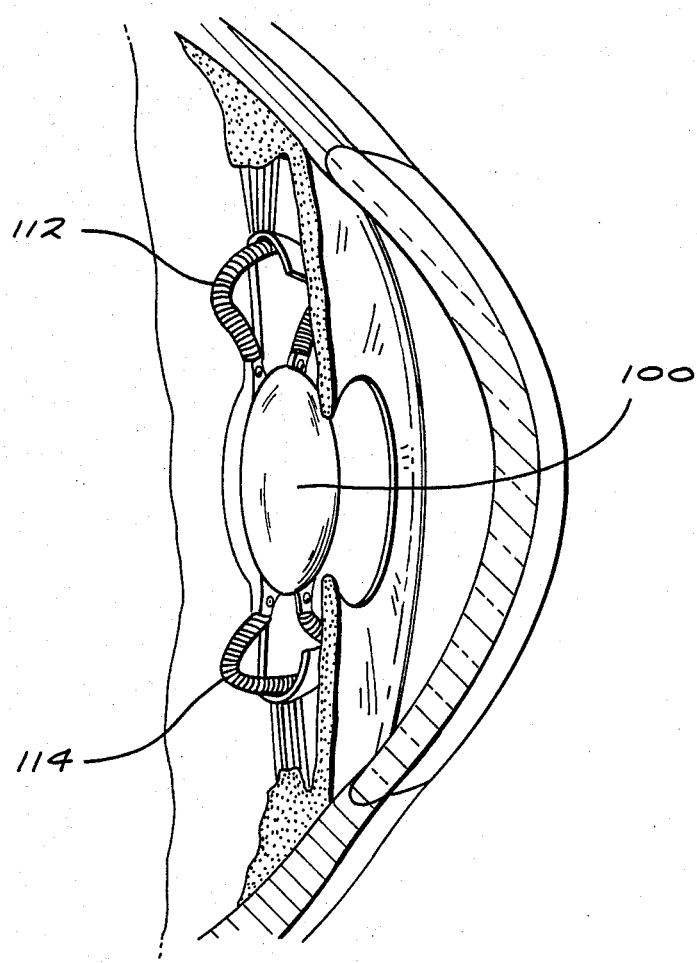
FIG. 8 illustrates a cross-sectional view of the intraocular lens of the present invention as inserted into the eye and within the lens capsule.

FIGS. 5, 6, 7 and 8 illustrate the first embodiment of the present invention located within the interior of the eye and with FIG. 6 illustrating a cross-sectional view of the intraocular lens of the present invention in the anterior position, with FIG. 7 illustrating a cross-sectional view of the intraocular lens of the present invention in the posterior position and FIG. 8 illustrating a cross-sectional view of the intraocular lens of the present invention within the lens capsule. FIG. 5 illustrates the lens in the central position viewed from the front and may represent the intraocular lens in either of the anterior, posterior or lens capsule positions.

As shown in FIG. 5, the central lens portion 100 is accurately centered in the eye and the coil spring loops 112 and 114 conform to either the anterior or posterior chamber positions or in the lens capsule. Even with a distortion of the coil spring loops 112 and 114, as shown in FIG. 5, the outward pressure is distributed evenly over a large number of points representing the outside surfaces of the coils.

FIGS. 6 and 7 show the intraocular lens inserted into the eye and with the lens portion 100 centered in the eye and supported in either the anterior or posterior chambers using the coil loops 112 and 114. As indicated above and shown in general in FIG. 5 and specifically in FIG. 8 the intraocular lens may also be located within the natural lens capsule after the removal of the lens nucleous. Again as indicated above, the coil loops conform to the curvature of either of the anterior or posterior chambers and or to the curvature of the I.D. of the lens capsule provide for an even distribution of pressure over the chamber surface.

It can be seen therefore that the coil spring loops of the present invention eliminate a serious deficiency of the prior art intraocular lenses. Specifically, the coil spring loops eliminate the problem of excess pressure which can occur in either the anterior or posterior chambers or in the lens capsule when the chamber is contacted at too small a number of points; usually, at one fine point only. This excess pressure could cause potential wounding of the eye structure and may also cause a tenderness in the eye area. If on the other hand the intraocular lenses are designed with too resilient a loop structure, this may reduce the pressure but may allow the lens to move around which can cause irritation and potentially blurred vision. The coil spring loops of the present invention overcome these and other deficiencies and allow for a more satisfactory intraocular lens implant. In addition, because the coil spring loop is so flexible and adjusts to so many different surface shapes of the chambers, the number of sizes of intraocular lenses that is necessary may be greatly reduced and it may even be possible to use a single size for almost all patients.

It should be appreciated that although the invention has been described with reference to particular embodiments, other adaptations and modifications may be made. For example, the coil spring loops may be attached to the lens using other techniques and the lenses themselves may take different forms including foldable lenses. In addition, although the coil spring loops have been shown to be uniformly wound helixes of uniform diameter and made of filament of uniform thickness, the helixes do not necessarily have to be uniformly wound and uniform in diameter and the filament may have differing thickness.

For example, the helixes can be tapered so that the coil spring has a smaller or larger diameter at the ends and the spacing between the coils may also be varied if desired. In addition, the thickness of the filament material may be varied, if desired to produce particular flexible characteristics for the coil spring loop. In each instance, however, the desired result is to provide for a relatively uniform pressure exerted by the coil spring loop at a great number of points so as to distribute the pressure in the anterior or posterior chambers without any one or small number of points receiving excess pressure.

Because the pressure of the coil spring loops are distributed uniformly over a great number of points, this allows the coils to have a high degree of flexibility to maintain the lens in the central position while at the same time, the lens is prevented from moving which movement could cause blurred vision.

Although the invention has been described with reference to particular embodiments, it is to be appreciated that various adaptations and modifications may be made and the invention is only to be limited by the appended claims.

I claim:

1. An intraocular lens adapted to be implanted within an eye adjacent the iris of the eye in either the anterior or posterior position or in the lens capsule, including,
   a lens portion,
   at least one flexible fixation means carried by the lens portion for supportive engagement with the eye structure in either the anterior or posterior position or in the lens capsule to centrally position the lens portion within the eye structure, and
   the at least one flexible fixation means formed as a flexible loop attached to the lens portion and with the loop formed by a coil spring including a large plurality of adjacent turns to form a helix for distributing the supportive engagement with the eye structure over a large number of the turns of the helix.

2. The intraocular lens of claim 1 including two flexible fixation means carried by the lens portion and extending from opposite sides of the lens portion.

3. The intraocular lens of claim 1 wherein the lens portion includes at least two post portions and with the ends of the coil spring loop attached to and seated on the post portions.

4. The intraocular lens of claim 1 wherein the lens portion include at least one flange portion having an opening to receive and secure the ends of the coil spring loop.

5. The intraocular lens of claim 1 wherein the coil spring loop has the ends of the helix attached to the lens portion.

6. The intraocular lens of claim 1 wherein the helix is uniform in diameter.

7. The intraocular lens of claim 1 wherein the helix is formed of filament material of uniform thickness.

8. The intraocular lens of claim 1 wherein the coil spring loop is formed of plastic filament material.

9. The intraocular lens of claim 8 wherein the plastic filament material is polypropylene.

10. An attachment means for use with a lens portion of an intraocular lens of the type adapted to be implanted within an eye adjacent the iris of the eye in either the anterior or posterior position or in the lens capsule, the attachment means including,
    at least one flexible fixation means carried by the lens portion for supportive engagement with the eye structure in either the anterior or posterior postion or in the lens capsule to centrally position the lens portion within the eye structure, and
    the at least one flexible fixation means formed as a flexible loop attached to the lens portion and with the loop formed by a coil spring including a large plurality of adjacent turns to form a helix for distributing the supportive engagement with the eye structure over a large number of the turns of the helix.

11. The attachment means of claim 10 including two flexible fixation means carried by the lens portion and extending from opposite sides of the lens portion.

12. The attachment means of claim 10 wherein the lens portion includes at least two post portions and with the ends of the coil spring loop for attachment to and seating on the post portions.

13. The attachment means of claim 10 wherein the lens portion includes at least one flange portion having an opening and with the ends of the coil spring loop for reception by the opening.

14. The attachment means of claim 10 wherein the coil spring loop has the ends of the helix for attachment to the lens portion.

15. The attachment means of claim 10 wherein the helix is uniform in diameter.

16. The attachment means of claim 10 wherein the helix is formed of filament material of uniform thickness.

17. The attachment means of claim 10 wherein the coil spring loop is formed of plastic filament material.

18. The attachment means of claim 17 wherein the plastic filament material is polypropylene.

* * * * *